US011278524B2

(12) United States Patent
Tang et al.

(10) Patent No.: US 11,278,524 B2
(45) Date of Patent: Mar. 22, 2022

(54) FORMULATIONS AND METHODS FOR THE TREATMENT OF CANCERS

(71) Applicant: Stemirna (Shanghai) Biotechnology Co. LTED., Shanghai (CN)

(72) Inventors: Dean G. Tang, Williamsville, NY (US); Xin Chen, Wuhan (CN)

(73) Assignee: STEMIRNA (SHANGHAI) BIOTECHNOLOGY CO. LTED., Shanghai (CN)

( * ) Notice: Subject to any disclaimer, the term of this patent is extended or adjusted under 35 U.S.C. 154(b) by 0 days.

(21) Appl. No.: 16/825,104

(22) Filed: Mar. 20, 2020

(65) Prior Publication Data

US 2020/0222368 A1    Jul. 16, 2020

Related U.S. Application Data

(63) Continuation of application No. 15/888,962, filed on Feb. 5, 2018, now abandoned.

(51) Int. Cl.
| | |
|---|---|
| *A61K 31/4166* | (2006.01) |
| *A61P 35/00* | (2006.01) |
| *A61K 31/4709* | (2006.01) |
| *A61K 31/551* | (2006.01) |
| *A61K 31/496* | (2006.01) |
| *A61K 31/437* | (2006.01) |

(52) U.S. Cl.
CPC .......... *A61K 31/4166* (2013.01); *A61P 35/00* (2018.01); *A61K 31/437* (2013.01); *A61K 31/4709* (2013.01); *A61K 31/496* (2013.01); *A61K 31/551* (2013.01); *A61K 2300/00* (2013.01)

(58) Field of Classification Search
CPC .. A61K 31/58; A61K 31/496; A61K 31/4166; A61K 31/437; A61K 31/4709; A61K 31/551; A61P 35/00
See application file for complete search history.

(56) References Cited

U.S. PATENT DOCUMENTS

2019/0240198 A1   8/2019  Tang et al.
2020/0281949 A1*  9/2020  Warner ............... A61K 9/0053

FOREIGN PATENT DOCUMENTS

WO   WO 2017/216772 A2     12/2017
WO   WO-2017216772 A2 *   12/2017  ........... A61K 31/337

OTHER PUBLICATIONS

Clinical trial NCT01828476 published Apr. 10, 2013 (Year: 2013).*
Chen (Molecular Cancer Therapeutics vol. 10, pp. 2340-2349 (2011)) (Year: 2011).*
Rycaj et al. (Oncotarget vol. 7 pp. 14220-14240 published online Feb. 10, 2016). (Year: 2016).*
Enzalutamide. CAS Registry. Published 2020 (Year: 2020).*
ABT 199, CAS Registry, 2019, 1 page.
Evangelisti et al., "Therapeutic potential of targeting mTOR in T-cell acute lymphoblastic leukemia (Review)," International Journal of Oncology, 2014, vol. 45, pp. 909-918.
MDV 3100, CAS Registry, Dec. 10, 2006, 1 page.
Rycaj et al., "Longitudinal tracking of subpopulation dynamics and molecular changes during LNCaP cell castration and identification of inhibitors that could target the PSA-/lo castration-resistant cells," Oncotarget, 2016, vol. 7, pp. 14220-14240.

* cited by examiner

*Primary Examiner* — Theodore R. Howell
*Assistant Examiner* — George W Kosturko
(74) *Attorney, Agent, or Firm* — Cooley LLP

(57) ABSTRACT

The present invention is directed to a formulation for treating cancer comprising an androgen receptor signaling inhibitor and a B-cell-lymphoma-2 inhibitor, which may further comprising a Bromodomain-and-Extra-Terminal protein inhibitor or a phosphoinositide 3-kinase inhibitor.

19 Claims, 9 Drawing Sheets

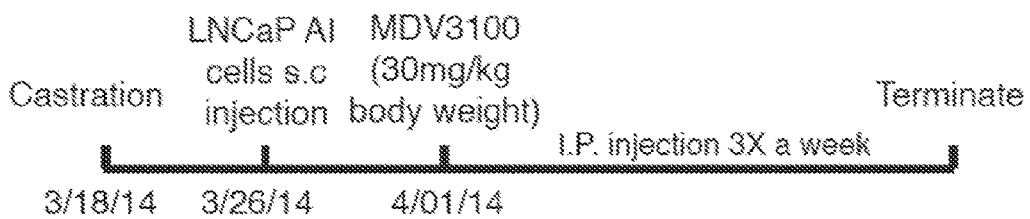
FIG. 3A
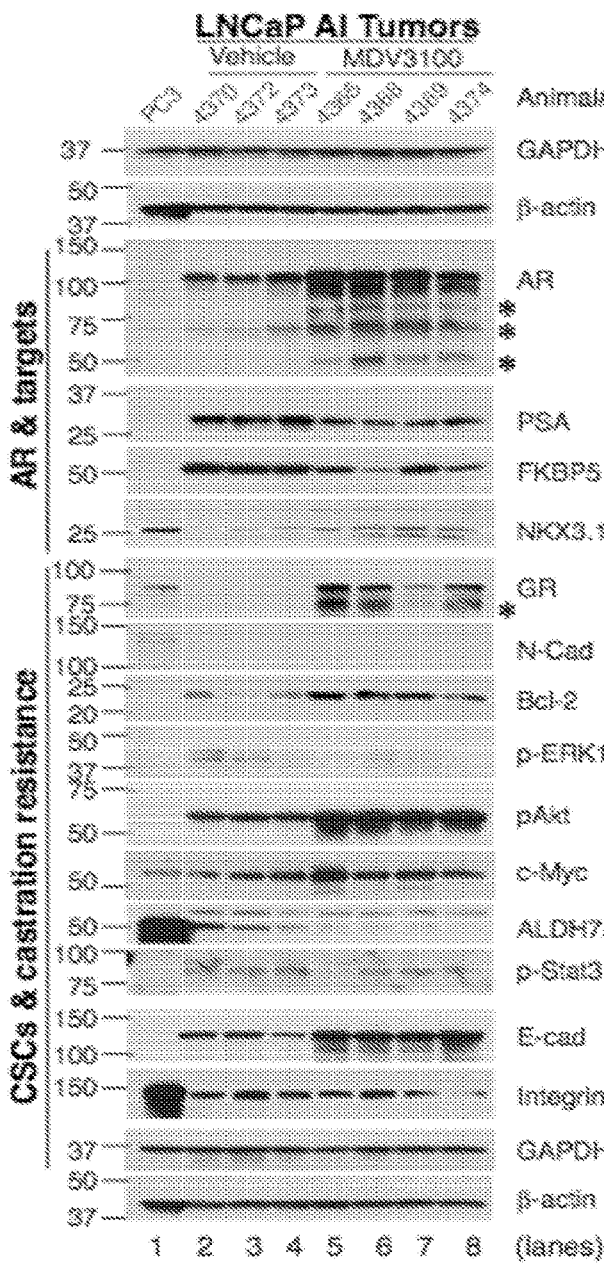
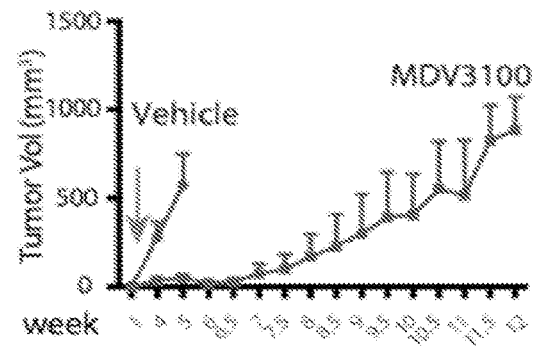
FIG. 3B
FIG. 3C

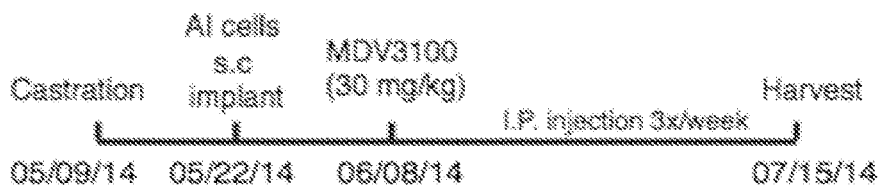
FIG. 4A
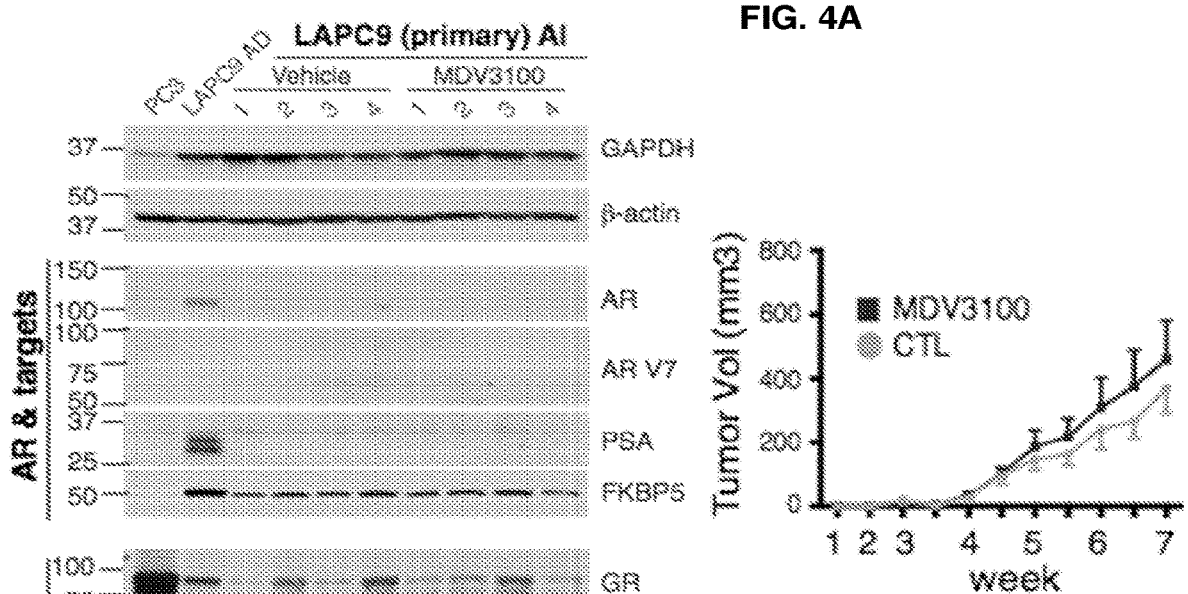
FIG. 4B
FIG. 4C

FORMULATIONS AND METHODS FOR THE TREATMENT OF CANCERS

CROSS REFERENCE TO RELATED APPLICATIONS

This application is a continuation of U.S. application Ser. No. 15/888,962 filed Feb. 5, 2018 which is incorporated by reference herein in its entirety for all purposes.

BACKGROUND OF THE INVENTION

Field of the Invention

The present invention relates generally to methods for the treatment of cancer. More specifically, the invention relates to methods of treating cancers, such as, using a combination therapy.

Description of the Related Art

Prostate cancer is an androgen-fueled malignancy and the androgen receptor (AR) represents the prime therapeutic target. However, androgen deprivation therapies (ADT) including chemical castration and use of androgen receptor antagonists have had limited success, since the targeted tumors become refractory to treatment and progress into castration resistant prostate cancer. Although many mechanisms have been reported to contribute to castration resistance, the origins of the castration resistant prostate cancer cell or the interactions between heterogeneous subpopulations of prostate cancer cells contributing to castration resistant prostate cancer remain poorly understood.

An analysis of >20 normal human prostate epithelial strains aimed at elucidating the precursor cells to human prostate cancer determined that primary, normal human prostate cells are AR– PSA– CD44+ 2 1+ CK5+ CK18+ progenitors that express the stem cell markers hTERT, p63, CD44, and Bcl-2, and regenerate prostate in vivo. Significantly, these progenitor cells can be transformed using a combination of androgen receptors, AKT, and ERG, suggesting that these cells can function as the cell of origin for human prostate cancer. On the other hand, lineage-tracing studies in the mouse prostate indicate that luminal cells function as the preferred transformation targets.

Cellular heterogeneity of human prostate cancer has been examined using cell and xenograft models, and >220 primary human prostate cancer (HPCa) derived cells and early-generation xenografts (patient derived xenografts) have been identified. These studies established that all prostate cancer cells are not functionally equal. For example, a subpopulation of prostate cancer cells, operationally termed prostate cancer stem cells (PCSCs), having stem cell gene expression profiles are endowed with enhanced tumorigenic and metastatic potential. Furthermore, prostate cancer cell population that lacks the differentiation marker Prostate Specific Antigen) ($PSA^{-/lo}$), harbors long-term castration-resistant tumor-propagating properties. Interestingly, a fraction (5-18%) of these cells undergo asymmetric cell division (ACD), a fundamental trait in adult stem cells. The $PSA^{-/lo}$ PCa cells are further enriched in epigenetic profiles such as bivalent chromatin domains, another well-established feature of stem cells. This is important from a clinical perspective since, $PSA^{-/lo}$ prostate cancer cells are heterogenous and can initiate robust tumor regeneration in androgen ablated individuals and mediate tumor recurrence during persistent castration, thereby functioning as a cell of origin for castration resistant prostate cancer.

Many of the PCSCs reported have low androgen receptor ($AR^{-/lo}$) expression, making them inherently resistant to androgen deprivation therapies. For instance, the $PSA^{-/lo}$ PCSC population is highly enriched in $AR^{-/lo}$ cells and readily propagates castration resistant prostate cancer. Still others have shown that the prostate cancer stem cell phenotype is induced by STAT3 dependent loss of androgen receptors, implying that, signaling through STAT3 and receptor tyrosine kinases, RAS/MAPK, PI3K/PTEN/AKT/mTOR may all regulate prostate cancer and castration resistance by reprogramming bulk prostate cancer stem cells.

Immunohistochemical studies (IHC) have revealed that; (1) androgen receptor and PSA protein expression in prostate cancer is both heterogeneous and discordant (that is, $AR^+PSA^-$, $AR^+PSA^+$, $AR^-PSA^-$, and/or $AR^-PSA^+$ phenotypes); (2) $AR^{-/lo}$ and/or $PSA^{-/lo}$ prostate cancer cells tend to increase in advanced, metastatic and recurrent tumors; and (3) poorly differentiated prostate cancer often completely lack $PSA^+$ prostate cancer cells. These observations are in agreement with other studies showing that high-grade and metastatic prostate cancers have an attenuated androgen-signaling signature, recurrence is associated with low PSA mRNA in prostate cancer cells, and, discordant androgen receptor and/or PSA expression manifest into differential sensitivities to ADT and other therapeutics. Heterogeneity in androgen receptor expression is further emphasized by observations that ~25% of the castration resistant prostate cancer samples completely lacked androgen receptor expression. The remainder $AR^+$ tumor population had highly heterogeneous androgen receptor expression; with both $AR^+$ and $AR^{-/lo}$ areas either intermingled with or frequently separated from each other. Among the $AR^+$ population, androgen receptor expression showed heterogeneity in subcellular localization classified into, exclusively nuclear (nuc-AR), exclusively cytoplasmic (cyto-AR), and a combination of the above (nuc/cyto-AR).

For example, transitioning of the PCa xenograft models, LAPC9, LAPC4, LNCaP, and VCaP, from androgen-dependent (AD) to androgen-independent (AI) states during propagation in castrated mice resulted in the androgen-independent tumors displaying nuc-AR (LNCaP), cyto-AR (LAPC4), nuc/cyto-AR (VCaP) and $AR^{-/lo}$ (LAPC9) phenotypic patterns, reminiscent of the clinical castration resistant prostate cancer manifestation. Since different androgen receptor-expressing patterns are likely to confer differential sensitivities to endocrine therapy in prostate cancer cells, a personalized approach that considers androgen receptor-expression status described above, would be central for successful treatment.

Androgen deprivation therapy remains the primary therapeutic approach in the treatment of prostate cancer. There are currently two approaches to androgen deprivation therapy—chemical "castration" using GnRH agonists such as goserelin to block testicular androgens or anti-androgens such as 4-(3-(4-Cyano-3-(trifluoromethyl)phenyl)-5,5-dimethyl-4-oxo-2-thioxoimidazolidin-1-yl)-2-fluoro-N-methylbenzamide (Enzalutamide) to block androgen receptor functions. Unfortunately, these approaches have not led to clinically acceptable remission since, many prostate cancer patients undergoing androgen deprivation therapy eventually become refractory to the treatment, progressing into advanced castration resistant prostate cancer, which is insensitive to this line of treatment. There is hence the need for new, patient centric, personalized treatment approaches in castration resistant prostate cancer.

Overall, there is a deficiency in the art for combinatorial and/or synergistic approaches to treat cancers. The present invention fulfills this longstanding need and desire in the art.

SUMMARY OF THE INVENTION

The present invention is directed to a formulation for treating cancer comprising an androgen receptor signaling inhibitor and a B-cell-lymphoma-2 inhibitor. The present invention is directed to a related formulation further comprising a Bromodomain-and-Extra-Terminal protein inhibitor. The present invention is directed to another related formulation further comprising a phosphoinositide 3-kinase inhibitor.

The present invention also is directed to a method for inhibiting tumor growth in a castration resistant prostate cancer. The method comprises contacting cells in the tumor with a pharmacologically effective amount of one of the formulations described herein.

The present invention is directed further to a method for treating a prostate cancer in a subject in need of such treatment. The method comprises administering to the subject a pharmacologically effective amount of one of the formulations described herein.

The present invention is further directed to a method for treating a cancer in a subject in need of such treatment. The method comprises administering either sequentially or simultaneously to the subject a pharmacologically effective amount of an androgen receptor signaling inhibitor, a B-cell lymphoma 2 inhibitor, a Bromodomain and Extra-Terminal protein inhibitor, and a phosphoinositide 3-kinase inhibitor.

Other and further aspects, features, benefits, and advantages of the present invention will be apparent from the following description of the presently preferred embodiments of the invention given for the purpose of disclosure.

BRIEF DESCRIPTION OF DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1A shows heterogeneous expression of androgen receptor in a patient castration resistant prostate cancer (representative patient #13553). * marks denote androgen receptor-negative (neg) areas. Inset on top right shows negative control. Lower panels show 4 patterns of androgen receptor expression. FIG. 1B shows a schematic for xenograft model used to generate primary and secondary castration resistant prostate cancer. FIG. 1C shows androgen receptor immunohistochemistry for androgen dependent and androgen independent xenograft models. Note the four androgen receptor staining patterns (nuc, cyto, nuc/cyto, and neg).

FIG. 2A shows western blotting analysis of whole cell lysates from the LAPC9 AI (PC9) and LAPC4 (PC4) models. LNCaP cells were used as control for androgen receptor and PSA FIG. 2B shows western blotting analysis of whole cell lysates from VCaP and LNCaP models. LAPC9 AD tumor was run for comparison. Asterisk denotes, non-specific bands.

FIGS. 3A-3F show molecular changes in secondary LNCaP castration resistant prostate cancer in response to Enzalutamide. FIG. 3A shows the experimental timeline. FIG. 3B shows treatment response of the androgen-independent LNCaP tumors to Enzalutamide. The arrow indicates the time when Enzalutamide-resistant secondary castration resistant prostate cancer began to emerge. FIG. 3C shows WB analysis of the molecules indicated in 3-4 representative tumors treated with vehicle (corn oil) or Enzalutamide (both β-actin and GAPDH were used as loading controls). Asterisk denotes the androgen receptor and GR splice variants. FIG. 3D shows representative IHC images of androgen receptor, PSA, and GR in one each vehicle- and Enzalutamide-treated endpoint tumors. FIG. 3E shows timeline for a pilot secondary castration resistant prostate cancer treatment. FIG. 3F shows the endpoint tumor images with tumor incidence and tumor weights indicated on the right. The two small tumors in the rectangle box were harvested two weeks later than the rest.

FIGS. 4A-4G shows molecular changes in castration- and Enzalutamide-resistant LAPC9 tumors. FIG. 4A shows the experimental timeline. FIG. 4B shows treatment response of the primary androgen-independent LAPC9 tumors to Enzalutamide. FIG. 4C shows western blot analysis of the molecules indicated in 4 representative tumors treated with vehicle (corn oil) or Enzalutamide (both β-actin and GAPDH were used as loading controls). FIG. 4D shows Representative IHC images of androgen receptor, PSA, and GR in AD, vehicle- and Enzalutamide-treated endpoint tumors. FIG. 4E shows the timeline for a pilot secondary castration resistant prostate cancer treatment. FIG. 4F shows JQ1 and JQ1-α2β1 inhibitor inhibited the LAPC9 AI tumor growth. FIG. 4G shows endpoint tumor images with tumor incidence and mean tumor weights indicated on the right.

FIG. 5A shows subcellular fractionation shows mainly cytosolic localization of androgen receptors in LAPC4 androgen-independent tumors (compare lanes 1 and 2) and cytosolic androgen receptors can be immunoprecipitated down by an anti-AR N-terminus Ab. Bracket and * indicate low M.W species AR variants. Cyto, cytosol; NE, nuclear extract. FIG. 5B shows timeline of therapeutic experiments. FIG. 5C shows treatment response of the LAPC4 primary androgen-independent tumors to Enzalutamide. FIG. 5D shows representative IHC images of androgen receptor and PSA in AD, vehicle- and Enzalutamide-treated endpoint tumors. FIG. 5E shows western blot analysis of the molecules indicated in 4 representative tumors (each) treated with vehicle (corn oil) or Enzalutamide (both β-actin and GAPDH were used as loading controls).

DETAILED DESCRIPTION OF THE INVENTION

Figure 1A:
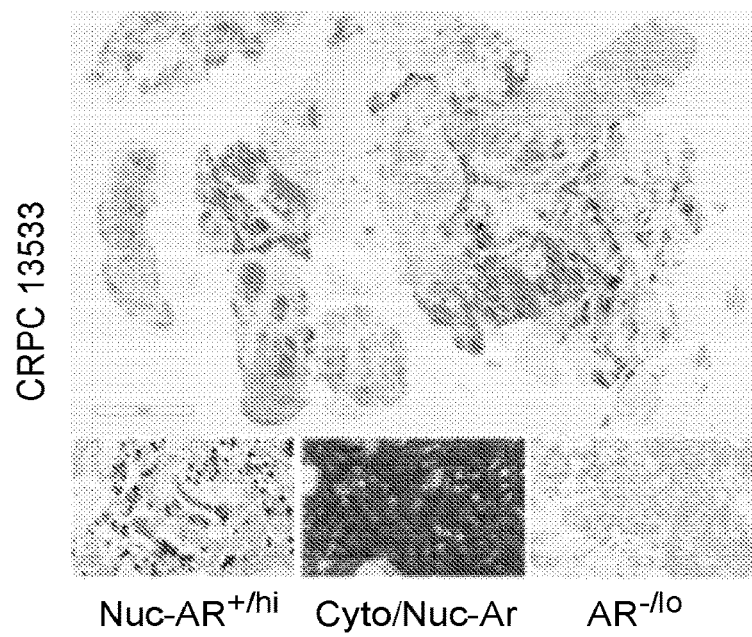
FIGS. 1A-1C shows androgen receptor heterogeneity in prostate cancer cells.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "contacting" refers to any suitable method of bringing the formulation described herein or one or more of its components into contact with a tumor or a cell comprising the same. In vitro or ex vivo this is achieved by exposing the comprising the same to the formulation or components thereof in a suitable medium. For in vivo applications, any known method of administration is suitable as described herein.

In one embodiment of the present invention, there is provided a formulation comprising, an androgen receptor signaling inhibitor and a B-cell-lymphoma-2 inhibitor. Androgen receptor signaling inhibitors may include, but are not limited to, enzalutamide, or other equivalent inhibitors, drugs or agents. In one aspect of this embodiment, the androgen receptor signaling inhibitor is enzalutamide contained in the formulation in an amount of about 5 mg/ml to about 10 mg/ml. B-cell-lymphoma-2 inhibitors may include, but are not limited to, venetoclax or other such inhibitors, drugs or agents. In one aspect of this embodiment, the B-cell-lymphoma-2 inhibitor is venetoclax contained in the formulation in an amount of about 10 mg/ml to about 15 mg/ml.

This embodiment also provides a formulation comprising, an androgen receptor signaling inhibitor, a B-cell-lymphoma-2 inhibitor, and a Bromodomain-and-Extra-Terminal protein inhibitor. Possible androgen receptor signaling inhibitors and B-cell-lymphoma-2 inhibitors are as described supra. Bromodomain-and-Extra-Terminal protein inhibitors may include, but are not limited to, JQ1, or other equivalent protein inhibitors, drugs or agents. In one aspect of this embodiment, enzalutamide and venetoclax may be contained at concentrations described supra, and JQ1 may be contained in the formulation in an amount of about 10 mg/ml to about 15 mg/ml.

This embodiment further provides a formulation comprising, an androgen receptor signaling inhibitor, a B-cell-lymphoma-2 inhibitor, and a phosphoinositide 3-kinase inhibitor. Possible androgen receptor signaling inhibitors and B-cell-lymphoma-2 inhibitors are as described supra. Phosphoinositide 3-kinase inhibitors may include, but are not limited to, NVP-BEZ235, or other equivalent inhibitors, drugs or agents. In one aspect of this embodiment, enzalutamide, venetoclax and NVP-BEZ235 may be contained at a concentration described supra.

This embodiment provides yet another formulation comprising, an androgen receptor signaling inhibitor, a B-cell-lymphoma-2 inhibitor, a Bromodomain-and-Extra-Terminal protein inhibitor and a phosphoinositide 3-kinase inhibitor. Representative examples of inhibitors from each class that may comprise this formulation is described supra. It is well within the skill of an artisan to determine the dosage of each inhibitor in the formulation.

In this embodiment further provided is a pharmaceutical composition comprising the formulation described supra and a physiologically acceptable carrier and/or excipient. Representative examples of pharmaceutical carriers include but are not limited to oil, suspension, spray, solution, nanoparticle, liposome, microcapsule, delivery device, or powder as known in the art. The pharmaceutical composition may be administered via oral or parenteral routes, such as subcutaneous, intravenous, intraperitoneal, intradermal, intranasal, or intramuscular routes.

The pharmaceutical composition may be administered one or more times to achieve a therapeutic effect. It is well within the skill of an artisan to determine dosage or whether a suitable dosage comprises a single administered dose or multiple administered doses. An appropriate dosage depends on the subject's health, the progression or remission of the disease, the route of administration and the formulation used.

In another embodiment there are provided methods for inhibiting growth of a castration resistant prostate cancer. In one aspect, the method comprises the step of contacting cells in the tumor with a pharmacologically effective amount of the formulation of an androgen receptor signaling inhibitor and a B-cell lymphoma 2 inhibitor. In another aspect of this embodiment, the method comprises the step of contacting cells in the tumor with a pharmacologically effective amount of the formulation of an androgen receptor signaling inhibitor, a B-cell lymphoma 2 inhibitor and a Bromodomain and Extra-Terminal inhibitor. In yet another aspect of this embodiment, the method comprises the step of contacting cells in the tumor with a pharmacologically effective amount of the formulation of an androgen receptor signaling inhibitor, a B-cell lymphoma 2 inhibitor and a phosphoinositide 3-kinase inhibitor. In yet another aspect of this embodiment, the method comprises the step of contacting cells in the tumor with a pharmacologically effective amount of the formulation of an androgen receptor signaling inhibitor, a B-cell lymphoma 2 inhibitor, a Bromodomain and Extra-Terminal inhibitor and a phosphoinositide 3-kinase inhibitor. Representative examples of inhibitors from each class are described supra. It is further well within the skill of an artisan to determine the dosage of each inhibitor in the formulation.

In yet another embodiment there are provided methods for treating a prostate cancer in a subject in need of such treatment, comprising the step of administering to the subject a therapeutically effective amount of an androgen receptor signaling inhibitor and a B-cell-lymphoma-2 inhibitor.

This embodiment also provides a method for treating a prostate cancer in a subject in need of such treatment, comprising the step of administering to the subject a therapeutically effective amount of an androgen receptor signaling inhibitor, a B-cell-lymphoma-2 inhibitor and a Bromodomain-and-Extra-Terminal protein inhibitor.

This embodiment further provides a method for treating a prostate cancer in a subject in need of such treatment, comprising the step of administering to the subject a therapeutically effective amount of an androgen receptor signaling inhibitor, a B-cell-lymphoma-2 inhibitor and a phosphoinositide 3-kinase inhibitor.

This embodiment provides further still a method for treating a prostate cancer in a subject in need of such treatment, comprising the step of administering to the subject a therapeutically effective amount of an androgen receptor signaling inhibitor, a B-cell-lymphoma-2 inhibitor, a Bromodomain-and-Extra-Terminal protein inhibitor and a phosphoinositide 3-kinase inhibitor.

In one aspect of this embodiment, the prostate cancer is androgen dependent prostate cancer. In another aspect of this embodiment, the cancer is androgen independent prostate cancer. In yet another aspect of this embodiment, the cancer is androgen receptor negative prostate cancer. In yet another aspect of this embodiment, the cancer is castration resistant prostate cancer.

In yet another embodiment there is provided a method for treating a cancer in a subject in need of such treatment comprising the step of administering either sequentially or simultaneously to the subject a pharmacologically effective amount of an androgen receptor signaling inhibitor, a B-cell lymphoma 2 inhibitor, a Bromodomain and Extra-Terminal protein inhibitor, and a phosphoinositide 3-kinase inhibitor.

In this embodiment the androgen receptor signaling inhibitor is enzalutamide. Also in this embodiment the B-cell lymphoma 2 inhibitor is venetoclax. In addition in this embodiment the Bromodomain and Extra-Terminal protein inhibitor is JQ1. Further in this embodiment the phosphoinositide 3-kinase inhibitor is NVP-BEZ235.

In this embodiment the cancer is a prostate cancer, such as, but not limited to, a castration resistant prostate cancer. Dosages or concentrations of these inhibitors may be as described supra or may be other amounts as readily determined by one of ordinary skill in the art.

A person having ordinary skill in this art would readily able to determine the appropriate dosage for the androgen receptor signaling inhibitors, the B-cell-lymphoma-2 inhibitors, Bromodomain-and-Extra-Terminal protein inhibitors and the phosphoinositide 3-kinase inhibitors in the formulation described supra, useful to treat the indicated prostate cancer. A person having ordinary skill in this art would also be capable of determining the most effective routes of administration, which include but are not limited to, oral administration and intravenous administration. A person having ordinary skill in this art would further be able to determine the frequency of administration, which may be adjusted from once a week, to several times a week to every week day depending on the cancer being treated.

Thus, provided herein are formulations of inhibitors and other compounds and pharmaceutical compositions thereof effective for treating a cancer or inhibiting growth of cells or tumors associated with the prostate cancer. Representative compounds comprising the formulation may be:

The following examples are given for the purpose of illustrating various embodiments of the invention and are not meant to limit the present invention in any fashion.

Example 1

Figure 1B:
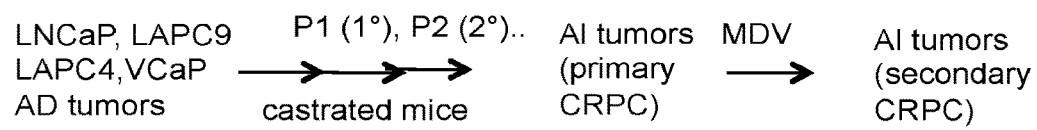
Figure 1C:
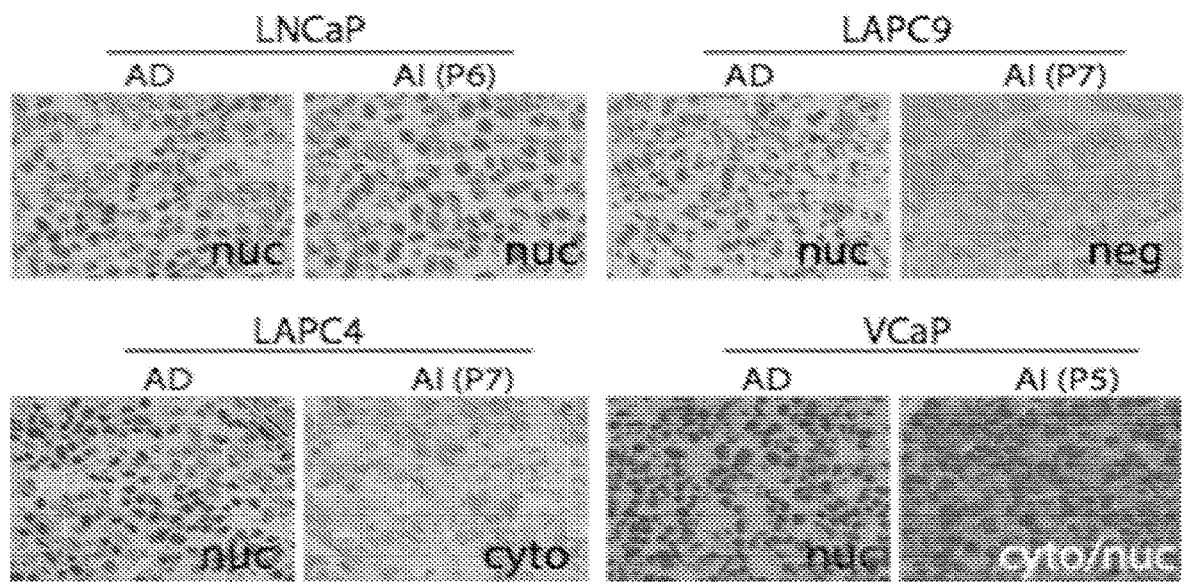

Patterns of AR Expression in Clinical Castration-Resistant Prostate Cancer and Castration-Resistant (CR) Xenografts About 100 castration resistant prostate cancer whole-mount (WM) or tissue microarray (TMA) slides were assayed for androgen receptor expression using two antibodies that recognize the N-terminal epitopes of the androgen receptor, which could detect both full-length androgen receptor and all c-terminal truncated androgen receptor variants. The results revealed interesting and striking heterogeneous patterns of androgen receptor expression. Of the tested clinical samples, 26 cases (25%) completely lacked androgen receptor expression. The remaining $AR^+$ tumors showed highly heterogeneous androgen receptor expression with both $AR^+$ and $AR^{-/lo}$ areas either inter-mingled with or frequently separated from each other (FIG. 1A). When 'zoomed' in, the androgen receptor-positive PCa cells showed 3 expression patterns: substantially nuclear (nuc-AR), substantially cytoplasmic (cyto-AR), and both nuclear and cytoplasmic (nuc/cyto-AR) (FIG. 1A, lower panel). When the PCa xenograft models—LAPC9, LAPC4, LNCaP, and VCaP, transitioned from androgen-dependent (AD) to androgen-independent (AI) state during propagation in castrated mice (FIG. 1B), the androgen-independent tumors displayed the 4 AR patterns resembling those observed in clinical castration resistant prostate cancer discussed above. Specifically, the LNCaP androgen-independent tumors showed substantially nuc-AR, LAPC4 showed substantially cyto-AR, VCaP showed nuc/cyto-AR, and LAPC9 showed substantially $AR^{-/lo}$ phenotypes (FIG. 1C).

Molecular Changes in Castration Resistant Prostate Cancer Induced by Surgical Castration The xenograft models—LAPC9, LAPC4, LNCaP, and VCaP were serially passaged in castrated male NOD/SCID-γ mice (NSG; for LNCaP or NOD/SCID for the other models). The tumors were then harvested for western blot analysis for

| Compound | Chemical name |
|---|---|
| Enzalutamide | -(3-(4-Cyano-3-(trifluoromethyl)phenyl)-5,5-dimethyl-4-oxo-2-thioxoimidazolidin-1-yl)-2-fluoro-N-methylbenzamide |
| Venetoclax | 4-(4-{[2-(4-Chlorophenyl)-4,4-dimethyl-1-cyclohexen-1-yl]methyl}-1-piperazinyl)-N-({3-nitro-4-[(tetrahydro-2H-pyran-4-ylmethyl)amino]phenyl}sulfonyl)-2-(1H-pyrrolo[2,3-b]pyridin-5-yloxy) benzamide |
| JQ1 | (S)-tert-butyl 2-(4-(4-chlorophenyl)-2,3,9-trimethyl-6H-thieno[3,2-f][1,2,4]triazolo[4,3-a][1,4]diazepin-6-yl)acetate |
| NVP-BEZ235 | 2-Methyl-2-{4-[3-methyl-2-oxo-8-(quinolin-3-yl)-2,3-dihydro-1H-imidazo[4,5-c]quinolin-1-yl]phenyl}propanenitrile |

Figure 2A:
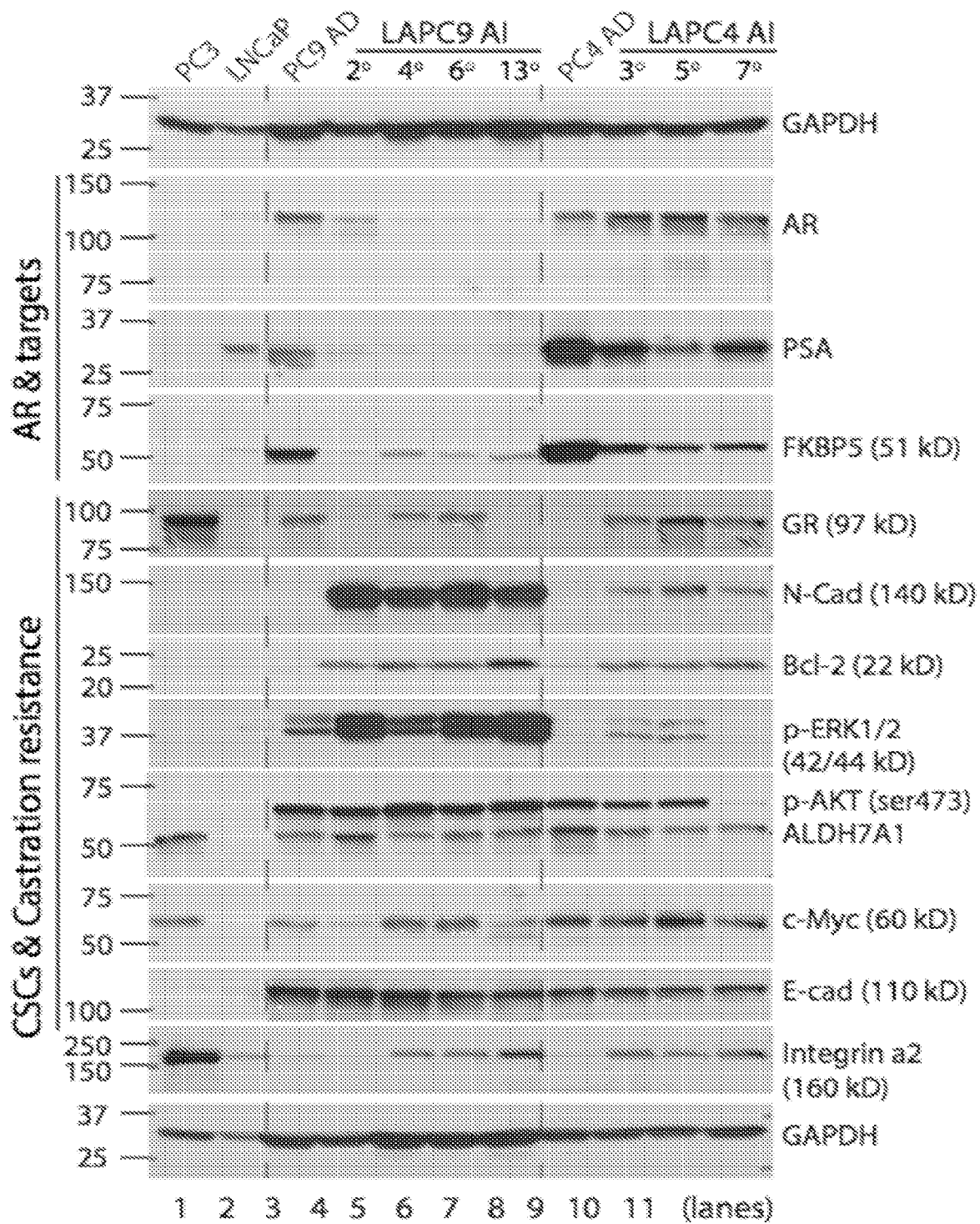
FIGS. 2A-2B shows western blot analysis of molecular changes in castration resistant prostate cancer induced by surgical castration.

As is well known in the art, the methods of the present invention may be administered to either human or non-human subjects. For example, administration may be oral or parenteral. As is well known in the art, the methods of the present invention may be administered alone or in combination with one or more other commonly used cancer chemotherapeutic agents to a subject to treat a particular condition.

androgen receptor, androgen receptor-target molecules, cancer stem cell (CSC) and castration resistance (CR) markers. PC3 cells were used as a negative control for androgen receptors. 60 μg of whole cell lysate was loaded in each lane. GADPH was run as the loading controls (top and bottom panels). FIG. 2A shows that castration led to a significant reduction of androgen receptors and its two targets PSA and FKBP5 in LAPC9 androgen-independent tumors. On the other hand, the LAPC9 primary androgen-independent tumors showed significant upregulation of 5 molecules/pathways: N-cadherin, Bcl-2, integrin α2, c-Myc, and p-ERK1/2. In contrast, markers, GR, pAkt, ALDH7A1 (57), and p-Stat3 did not show any difference between androgen-dependent and androgen-independent tumors (FIG. 2A). This enrichment of AR$^{-/lo}$/PSA$^{-/lo}$ PCa cells in LAPC9 androgen-independent suggests that they can function as the cell-of-origin for castration resistant prostate cancer.

Figure 2B:
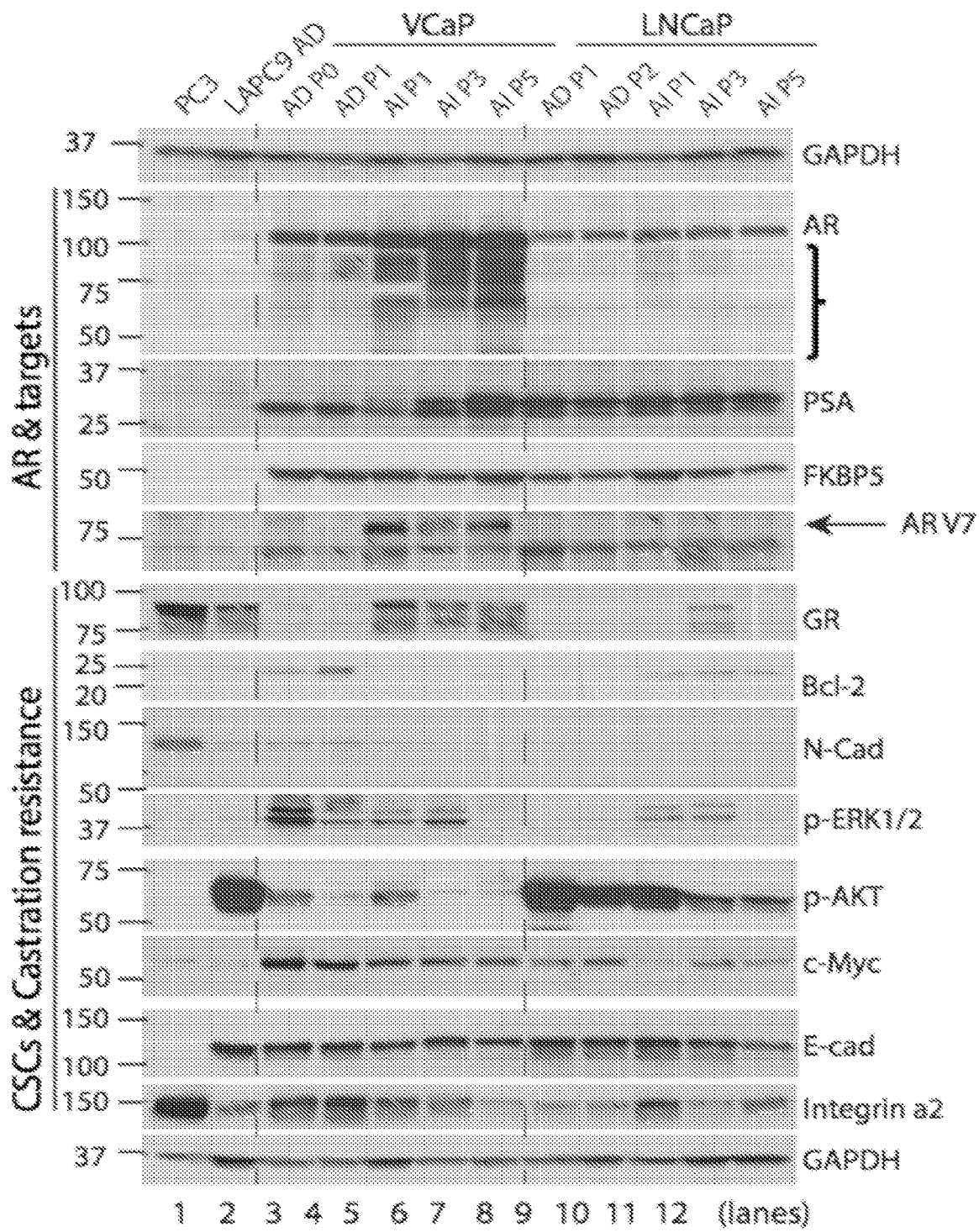

In the LNCaP model, castration led to increased androgen receptor expression (FIG. 2B), which was localized mostly in the nuclei (see FIG. 1C). The 3 androgen receptor target molecules, PSA, FKBP5, and NKX3.1, were expressed and no androgen receptor splice variants including AR-V7 were observed (FIG. 2B). Among the CSC and CR markers, N-cadherin was not detected; GR (glucocorticoid receptor) showed only transient and minimal changes; and c-Myc, E-cadherin, and p-AKT decreased slightly (FIG. 2B). In contrast, integrin α2 (CSC marker) and pERK1/2 showed initial increase followed by decline, whereas Bcl-2 and pStat3 demonstrated sustained increases (FIG. 2B).

Example 2

Figure 4D:
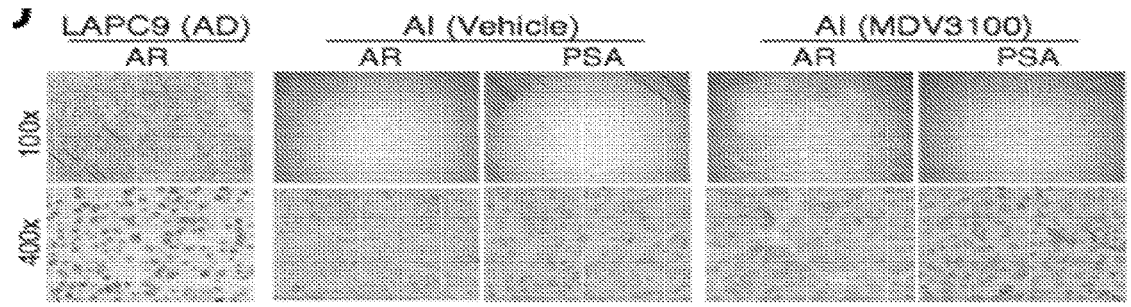

Molecular Changes in Secondary LNCaP Castration Resistant Prostate Cancer in Response to Enzalutamide Therapy To test the efficacy of enzalutamide in reducing androgen-independent PCa tumor burden, therapy experiments were performed by treating mice bearing LNCaP AI-tumors with enzalutamide, administered by i.p. route. FIG. 4B revealed that enzalutamide suppressed growth of androgen-independent LNCaP for the first 6.5 weeks, suggesting that the upregulated nuc-AR (see FIG. 1C) is causally mediating the primary castration resistant prostate cancer in the LNCaP androgen-independent-tumor model. However, at about 7 weeks no further response to enzalutamide was observed (arrow, FIG. 4B) suggesting the emergence of enzalutamide-resistant tumors. These secondary castration resistant prostate cancer tumors were resistant to both surgical castration and enzalutamide as evidenced by western blotting analysis (FIG. 4C) and immune-histochemical analysis (FIG. 4D) for markers, androgen receptor, GR, including. GR splice variants (FIG. 4C). Among the 3 androgen receptor targets, PSA (FIGS. 4C-4D) and FKBP5 (FIG. 4C) decreased, suggesting that in enzalutamide resistant secondary LNCaP CR tumors, androgen receptor binding to the genome is shifting away from conventional targets. The observed decrease in PSA is consistent with earlier observations that persistent castration leads to an enrichment in phenotypically undifferentiated PSA$^{-/lo}$ PCa cells.

Figure 4E:
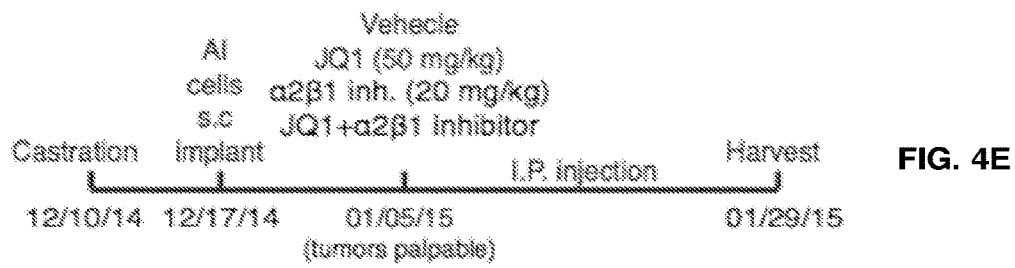
Figure 4F:
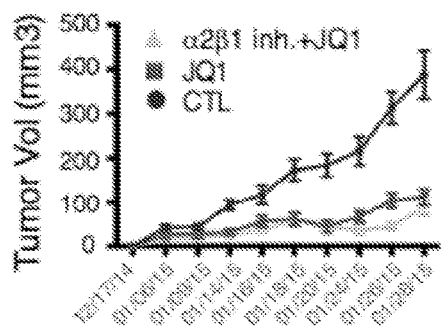

Molecular Changes in Secondary LNCaP Castration Resistant Prostate Cancer in Response to Enzalutamide/Venetoclax Combination Therapy Among the CSCs and castration resistance markers examined, Bcl-2 showed the most prominent upregulation in response to enzalutamide (FIG. 4C). To determine if therapeutic targeting of Bcl-2 in combination with Enzalutamide a targeted therapy experiment was performed by treating mice bearing LNCaP primary androgen-independent tumors simultaneously with enzalutamide and a Bcl-2 antagonist, venetoclax (FIG. 4E). The results shown in FIG. 4F demonstrate a clear and striking suppression of emergence (incidence) of LNCaP secondary castration resistant prostate cancer ($P<0.0001$, $\chi^2$ test) in animals administered Enzalutamide+Venetoclax combination therapy. In contrast, control combination experiments in which venetoclax was substituted with the GR antagonist, mifepristone (RU486), inhibited only inhibited tumor growth without reducing incidence (FIG. 4F).

Example 3

Figure 3D:
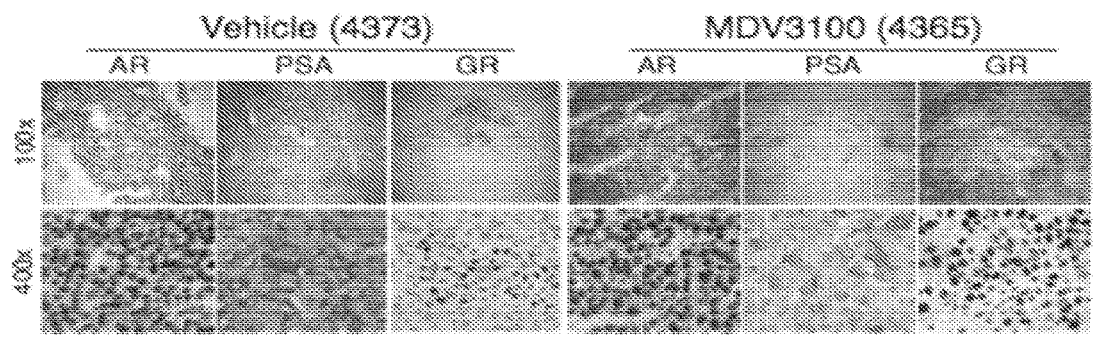
Figure 3E:
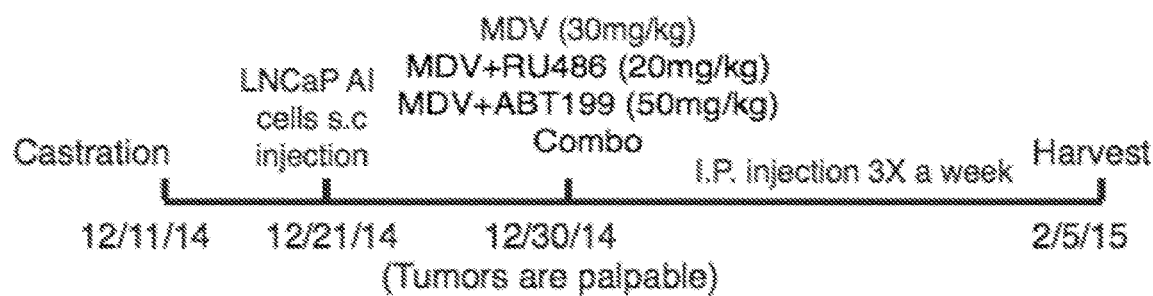
Figure 3F:
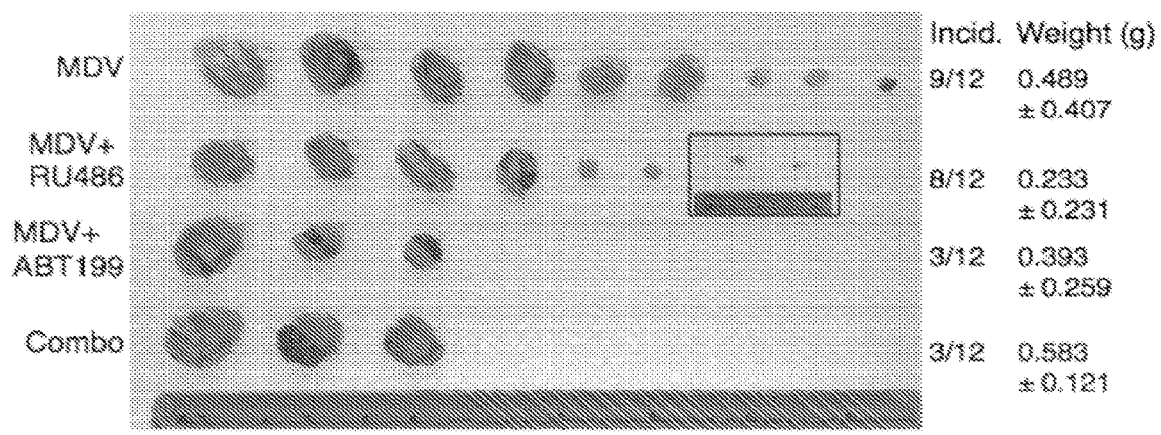
Figure 4G:
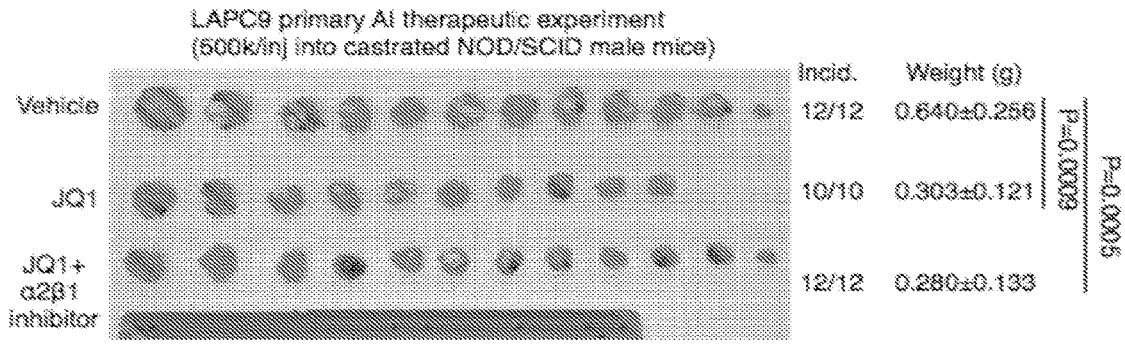

Castration of LAPC9 AD Tumors Leads to Decreased AR and Upregulation of Many CSC and Castration-Associated Molecules and Pathways To determine the sensitivity of LAPC9 androgen-independent tumors to enzalutamide, therapy experiments were performed as described for the LNCaP primary AI tumors (FIG. 3). FIG. 4 shows that in sharp contrast to the observed reductions in tumor volume following Enzalutamide therapy, LNCaP primary androgen-independent tumors were refractory to enzalutamide administration (FIG. 4B). Western blotting (FIG. 4C) and immuno-histochemical (FIG. 4D) analysis revealed no expression of androgen receptors and PSA. FKBP5 levels were greatly diminished in both vehicle and treatment groups. On the other hand Enzalutamide treatment continued to express high levels of integrin α2, c-Myc, N-cadherin, Bcl-2, and p-ERK1/2 (FIG. 4C). To determine whether blocking alternate pathways regulated by any of these high expressing proteins, in the Enzalutamide resistant LAPC9 androgen-independent tumors, affects tumor burden, therapy experiments were performed with the Bromodomain and Extra-Terminal protein (a upstream regulator of Myc transcription) inhibitor, JQ1. The integrin α2β1 inhibitor, Compound 15 (142,143) was used as a positive control. FIGS. 4F-4G shows that JQ1 significantly inhibited tumor growth but not tumor incidence (compare FIG. 4F with FIG. 3F). These studies show that Myc in the AR$^{-/lo}$ LAPC9 androgen-independent tumors is causally important for tumor growth under androgen-independent conditions, and further suggest the likely benefits of making a combinatorial formulation comprising Enzalutamide and JQ1 in the treatment of androgen-independent prostate cancer and castration resistant prostate cancer.

Example 4

Figure 5A:
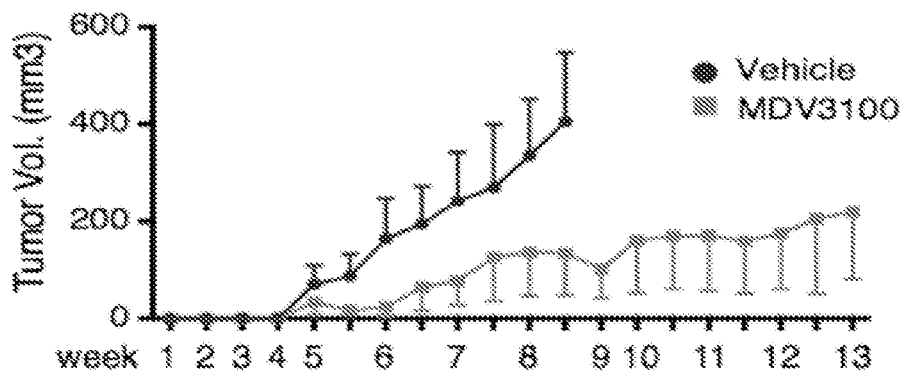
FIGS. 5A-5E shows molecular changes in castration- & Enzalutamide-resistant LAPC4 tumors.
Figure 5B:
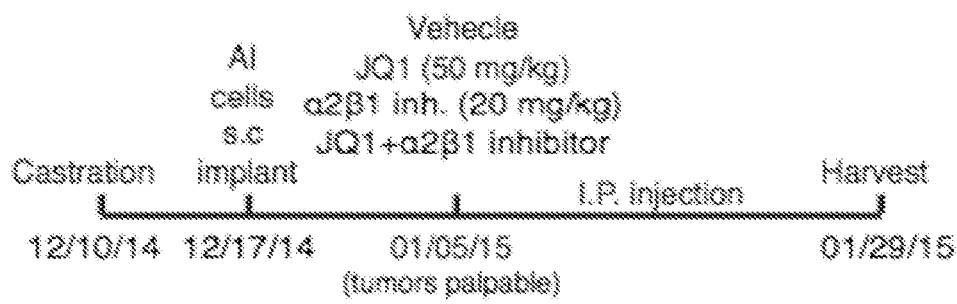

Response to Enzalutamide Treatment in LAPC4 AI Tumors Having Cytoplasmic AR Localization As shown in FIG. 1C, immuno-histochemistry analysis revealed significant cytoplasmic localization of ARs in LAPC4 androgen-independent tumors. This is further confirmed by subcellular fractionation followed by western blot analysis (FIG. 5A), which shows that a majority of androgen receptor was in the cytosol, with only a minor signal being attributed to the nuclear fraction (FIG. 5A lanes 1 vs. 2). To determine whether targeting cyt-AR in these tumors would be effective in reducing tumor burden, castrated mice bearing LAPC4 androgen-independent tumors were administered enzalutamide as indicated (FIG. 5B), and the tumor volume measured.

Figure 5C:
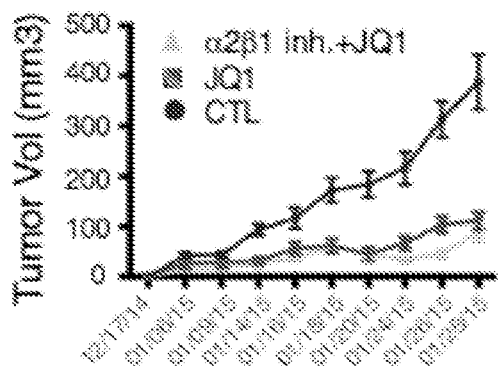
Figure 5D:
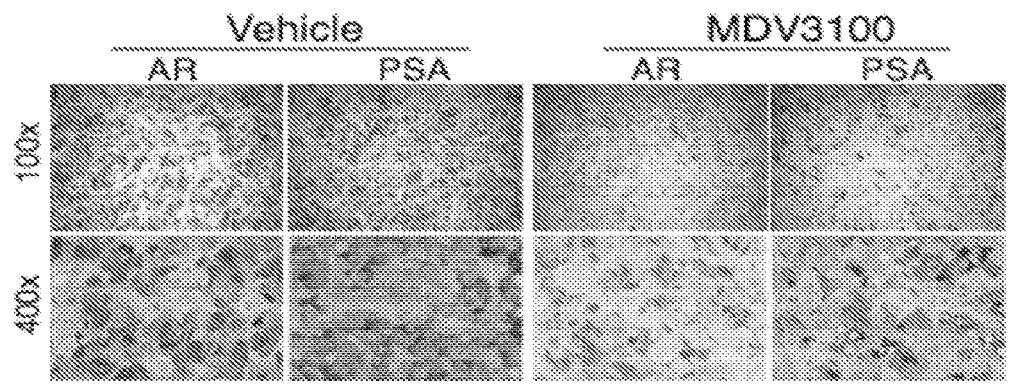
Figure 5E:
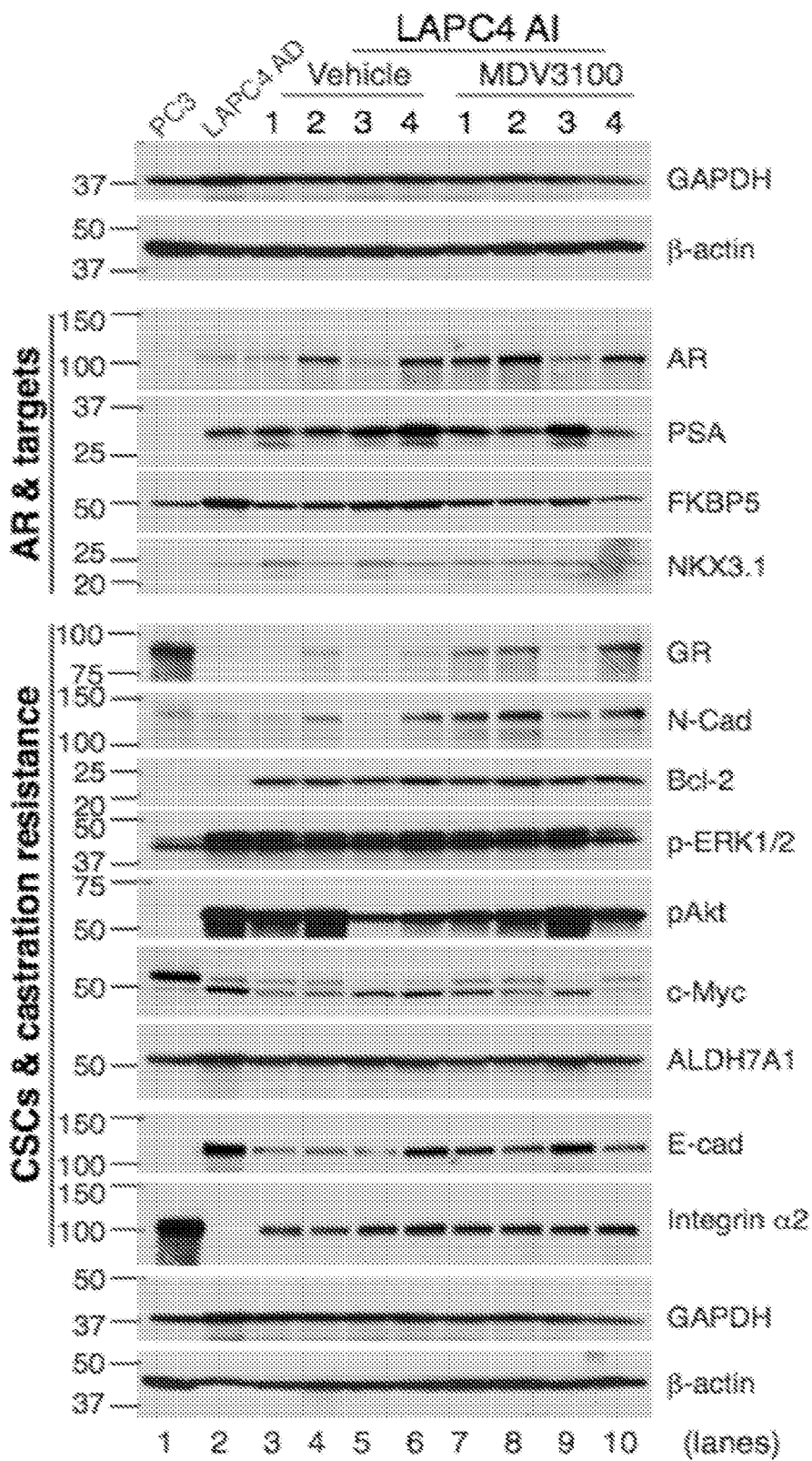

FIG. 5C shows that LAPC4 androgen-independent tumors in the enzalutamide treatment group grew significantly slower in the first 2-3 weeks compared to control groups that were administered only the vehicle, corn oil (FIG. 5C). However, starting from ~6.5-7 weeks, tumors resumed growth, indicative of resistance to enzalutamide. Interestingly, unlike the vigorous growth pattern of enzalutamide-resistant nuc-AR+ LNCaP tumors (FIG. 3C), the enzalutamide-resistant cyto-AR+ LAPC4 tumors grew relatively slow even up to 13 weeks (FIG. 5C). This slow growth was not due to relocation of androgen receptor to the nucleus, or resurgence in AD nu-AR+ tumors since immuno-histochemistry showed that androgen receptor was still largely in the cytoplasm (FIG. 5D). Western blot analysis revealed that the enzalutamide-resistant LAPC4 tumors continued to express high levels of GR, N-cadherin, Bcl-2, and integrin α2, with slight increases in E-cadherin expression FIG. 5E). This opens the possibility of employing combinatorial approaches that target androgen receptor (Enzalutamide) together molecules such as Bcl2 (Venetoclax).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A formulation, comprising:
an androgen receptor signaling inhibitor; and
a B-cell lymphoma 2 inhibitor, wherein the androgen receptor signaling inhibitor is enzalutamide, and wherein the B-cell lymphoma 2 inhibitor is venetoclax.

2. The formulation of claim 1, wherein enzalutamide is contained in said formulation in a concentration of about 5 mg/ml to about 10.0 mg/ml.

3. The formulation of claim 1, wherein venetoclax is contained in said formulation in a concentration of about 10 mg/ml to about 1 5 mg/ml.

4. A pharmaceutical composition comprising the formulation of claim 1 and a pharmaceutically acceptable carrier.

5. The formulation of claim 1, further comprising:
a Bromodomain and Extra-Terminal protein inhibitor.

6. The formulation of claim 5, wherein the Bromodomain and Extra-Terminal protein inhibitor is JQ1.

7. The formulation of claim 6, wherein JQ1 is contained in said formulation in a concentration of about 10 mg/ml to about 15 mg/ml.

8. A pharmaceutical composition comprising the formulation of claim 5 and a pharmaceutically acceptable carrier.

9. The formulation of claim 1, further comprising:
a phosphoinositide 3-kinase inhibitor.

10. The formulation of claim 9, wherein the phosphoinositide 3-kinase inhibitor is NVP-BEZ235.

11. A pharmaceutical composition comprising the formulation of claim 9 and a pharmaceutically acceptable carrier.

12. A method for inhibiting growth of a tumor in a castration resistant prostate cancer comprising the step of:
contacting cells in the tumor with a pharmacologically effective amount of a formulation, comprising: an androgen receptor signaling inhibitor and a B-cell lymphoma 2 inhibitor, wherein the androgen receptor signaling inhibitor is enzalutamide, and wherein the B-cell lymphoma 2 inhibitor is venetoclax.

13. The method of claim 12, wherein the formulation further comprises a Bromodomain and Extra-Terminal protein inhibitor.

14. The method of claim 12, wherein the formulation further comprises a phosphoinositide 3-kinase inhibitor.

15. A method for treating a prostate cancer in a subject in need of such treatment, comprising the step of:
administering to said subject a pharmacologically effective amount of a formulation comprising an androgen receptor signaling inhibitor and a B-cell lymphoma 2 inhibitor, wherein the androgen receptor signaling inhibitor is enzalutamide, and wherein the B-cell lymphoma 2 inhibitor is venetoclax.

16. The method of claim 15, wherein said inhibitors are administered sequentially or simultaneously.

17. The method of claim 15, further comprising:
administering to said subject a pharmacologically effective amount of a Bromodomain and Extra-Terminal protein inhibitor.

18. The method of claim 15, further comprising:
administering to said subject a pharmacologically effective amount of a phosphoinositide 3-kinase inhibitor.

19. The method of claim 15, wherein said prostate cancer is an androgen dependent prostate cancer, an androgen independent prostate cancer, an androgen receptor negative prostate cancer, or a castration resistant prostate cancer.

* * * * *